United States Patent [19]

Erwin

[11] Patent Number: 4,946,450

[45] Date of Patent: Aug. 7, 1990

[54] GLUCAN/COLLAGEN THERAPEUTIC EYE SHIELDS

[75] Inventor: Robert L. Erwin, San Francisco, Calif.

[73] Assignee: Biosource Genetics Corporation, Vacaville, Calif.

[21] Appl. No.: 341,012

[22] Filed: Apr. 18, 1989

[51] Int. Cl.$^5$ .................. A61M 35/00; A61F 2/00
[52] U.S. Cl. ..................... 604/294; 128/156; 523/106; 424/428
[58] Field of Search ............... 128/163, 156; 604/294; 523/105, 106, 113; 424/428

[56] References Cited

U.S. PATENT DOCUMENTS

| | | | |
|---|---|---|---|
| 3,963,025 | 6/1976 | Whitaker et al. | 424/428 |
| 4,164,559 | 8/1979 | Miyata et al. | |
| 4,264,155 | 4/1981 | Miyata | 523/106 |
| 4,713,446 | 12/1987 | Devore et al. | |
| 4,739,046 | 4/1988 | LiLuzio | |
| 4,761,402 | 8/1988 | Williams et al. | |
| 4,833,131 | 5/1989 | Williams et al. | 536/1.1 |

FOREIGN PATENT DOCUMENTS

| | | |
|---|---|---|
| 0214853 | 3/1987 | European Pat. Off. |
| 63-71192 | 3/1988 | Japan |

OTHER PUBLICATIONS

Abstract of Baxter et al., *Rad. Res. 51*, 540 (1972).
Abstract of Manners et al., *Biochem. J. 135*, 19 (1973).
Abstract of Manners et al., *Biochem. J. 135*, 31 (1973).
Abstract of Rubin et al., *J. Clin. Pharmacol. Aug.-Sep.*, 309 (1973).
Abstract of Mansell et al., *J. National Cancer Inst. 54*, 571 (1975).
Abstract of Mansell et al., *Ann. N.Y. Acad. Sci. 277*, 20 (1976).
Abstract of Sasaki et al., *Gann 67*, 191 (1976).
Abstract of Burgaleta, *Cancer Res. 37*, 1739 (1977).
Abstract of West, *Int. Arch. Allergy Appl. Immun. 56*, 155 (1978).
Abstract of West, *Int. Arch. Allergy Appl. Immun. 56*, 380 (1978).
Abstract of DiLuzio et al., *Int. J. Cancer 24*, 773 (1979).
Abstract of Lotzova et al., *J. Immunol. 123*, 607 (1979).
Abstract of Kanai et al., *Japan. J. Med. Sci. Biol. 33*, 283 (1980).
Abstract of Leibovich et al., *J. Reticuloendothel. Soc. 27*, 1 (1980).
Abstract of Kenyon, *Am. J. Vet. Res. 44*, 652 (1983).
Abstract of Williams et al., *Surgery 93*, 448 (1983).
Abstract of Wolk et al., *Medical Biology 63*, 73 (1985).
Abstract of Kay et al., *Ophthalmic Surg. 17*, 626 (1986).
Abstract of Sheets et al., *Amm. Ophthalmol. 18*, 297 (1986).
Abstract of Sherwood et al., *Int. J. Immunopharmac. 9*, 261 (1987).
Abstract of Kaufman, *J. Cataract Refract. Surg. 14*, 487 (1988).
Abstract of Poland et al., *J. Cataract Refract. Surg. 14*, 489 (1988).
Abstract of Aquavella et al., *J. Cataract Refract. Surg., 14*, 492 (1988).
Abstract of Marmer, *J. Cataract Refract. Surg. 14*, 496 (1988).
Abstract of Unterman et al., *J. Cataract Refract. Surg. 14*, 500 (1988).
Abstract of O'Brien et al., *J. Cataract Refract. Surg. 14*, 505 (1988).

*Primary Examiner*—Randall L. Green
*Assistant Examiner*—Paul Prebilic
*Attorney, Agent, or Firm*—Venable, Baetjer, Howard & Civiletti

[57] ABSTRACT

A therapeutic eye shield comprising from about 50% to about 80% collagen and from about 20% to about 50% glucan is disclosed. The collagen acts as a drug delivery system for the therapeutic agent, glucan. The therapeutic eye shields are useful for prophylaxis and treatment of eye infections particularly following ophthalmic surgery or wounding.

19 Claims, No Drawings

GLUCAN/COLLAGEN THERAPEUTIC EYE SHIELDS

FIELD OF THE INVENTION

The invention relates to therapeutic eye shields comprising a combination of glucan and collagen. Glucan, the therapeutic agent, is incorporated into a collagen shield which serves as the delivery system for the glucan to get to its target in the eye. The therapeutic eye shields may be used to treat eye infections or as a prophylactic measure following ophthalmologic surgery.

BACKGROUND OF THE INVENTION

The most common form of glucan is yeast glucan or *Saccharomyces cerevisiae* glucan. An additional form of glucan is lentinan from the Japanese mushroom, *Lentines edodes*.

Yeast glucan is isolated from the cell walls of *Saccharomyces cerevisiae*, and is a relatively high molecular weight (about 240,000) polysaccharide (Manners et al., *Biochem. J.* 135, 19 (1973)). Glucan is responsible for cell rigidity, and under a scanning microscope retains many of the morphological characteristics of yeast; i.e. it is a spheroid approximately 5 μm in diameter with a bud scar on each unit (Baxter et al., *Rad. Res.* 51, 540 (1972)). Glucan has a high proportion of β-(1-6)-glucosidic linkages (Manners et al., *Biochem. J.* 135, 31 (1973)). Glucan, in its natural state, is water insoluble, and x-ray diffraction studies have shown that glucan exists in the form of a triple-stranded helix (Sarko et al., *Biochem. Soc. Trans.* 11, 139 (1983)). Upon hydrolysis, glucan yields predominantly or completely, the monosaccharide, D-glucose (Manners et al., *Biochem. J.* 135, 19 (1973)).

Although naturally occurring glucan is water insoluble, at least two forms of water soluble glucan have been prepared. One form of water soluble glucan is a phosphorylated glucan described in U.S. Pat. Nos. 4,739,046 and 4,761,402. The other form of soluble glucan is prepared using the method of Sasaki et al., *Gann* 67, 191 (1976) as modified by DiLuzio et al., *Int. J. Cancer* 24, 773 (1979). These soluble glucans have the same general therapeutic effects of naturally occurring glucans, but are easier to use as injectable agents. Neither water soluble nor water insoluble glucans has been found to have good gelling properties. Therefore, glucans have not been used alone to make formed compositions.

Glucan has been recognized, therapeutically, as a macrophage activator (Wolk et al., *Medical Biology* 63, 73 (1985); Leibovich et al., *J. Reticuloendothel. Soc.* 27, 1 (1980); Williams et al., *Surgery* 93, 448 (1983); Burgaleta et al., *Cancer Res.* 37, 1739 (1977); Mansell et al., *J. Nat'l. Can. Inst.* 54, 571 (1975)). It has also been reported that glucan increases vascular permeability in the skin (West, *Int. Arch. Allergy Appl. Immun.* 56, 380 (1978)) and accelerates wound healing through the release of fibroblast-stimulating activity from monocytic macrophages (Kenyon, *Am. J. Vet. Res.* 44, 652 (1983)). Further reports of therapeutic uses for glucan include its administration to increase ganulocyte and macrophage production (Burgaleta et al., supra; Lotzova et al., *J. Immunol.* 123, 607 (1979)), its enhancement of interleukin-1, interleukin-2 and lymphokine production (Sherwood et al., *Int. J. Immunopharmac.* 9, 261 (1987)) and its anti-tumor and anti-staphylococcal activity (DiLuzio et al., *Int. J. Cancer* 24, 773 (1979)).

Additional reports describe glucan's enhancement of: phagocytic function (Wooles et al., *J. Reticuloendothel. Soc.* 1, 160 (1964)); humoral immunity (Williams et al., *J. Reticuloendothal. Soc.* 23, 479 (1978)); cell-mediated immunity (Wooles et al., *Science* 142, 1078 (1963)); serum complement levels (Haendchen et al., *Fed. Proc.* 40, 1151 (1981)); and macrophage secretory function (Kokoshis et al., *J. Reticuloendothal. Soc.* 25, 85 (1979)). Administration of glucan has also been shown to enhance hemopoietic activity including granulopoiesis, monocytopoiesis and erythropoiesis (Patchen, *Suru. Immunol. Res.* 2, 237 (1983)). Glucans have not been used for ophthalmic purposes or in ophthalmic preparations.

Like glucan, collagen is a relatively well-known composition. Collagen is a polypeptide substance of molecular weight about 130,000. Collagen comprises about one-third of the total protein in mammalian organisms, and is the main constituent of skin and connective tissue, and the organic substance of bone and teeth.

Although there are different types of collagen, all collagens are composed of molecules which contain three polypeptide chains (α chains) arranged in a triple helical configuration. The amino acid sequence of the α chains is mostly a repeating structure with glycine at every third position and proline or 4-hydroxyproline frequency preceding the glycine residues.

Collagen is differentiated from accompanying fibrous proteins (i.e. elastin and reticulin) by: (1) its content of proline, hydroxyproline and hydroxylysine; (2) the absence of tryptophan and its low tyrosine and sulfur contents; and (3) its high content of polar groups originating from the difunctional amino acids. These polar groups are responsible for swelling properties which lead to the dispersion of collagen in dilute acid. Denaturation of collagen comprises the conversion of the rigidly coiled helix to a random coil referred to as gelatin.

Collagen has been used as the fibers in sutures, and has been used in leather substitutes. In addition, collagen has been used as a gel in photographic emulsions, and has been used in coatings and in food casings.

Collagen has also been used in ophthalmic preparations. U.S. Pat. No. 4,713,446 describes a viscoelastic collagen solution of particular usefulness in ophthalmic surgery such as intracapsular and extracapsular cataract lens extraction, intraocular lens implantation, corneal transplant surgery and retinal detachment surgery. This viscoelastic collagen solution may also be used as a vitreous replacement.

Furthermore, collagen has been used ophthalmically in the form of collagen sponges or collagen shields. Kay et al., *Ophth. Surgery* 17, 626 (1986) describes the sub-tenon placement of a collagen sponge to deliver $^{57}$Co-bleomycin after glaucoma filtration surgery in rabbits. Sheets et al., *Ann. Ophthalmol.* 18, 297 (1986) describes the use of freeze-dried collagen eye patches in the treatment of inflammatory eye conditions.

Numerous authors describe the ophthalmic use of collagen shields with or without therapeutic agents. Kaufman, *J. Cataract Refract. Surg.* 14, 487 (1988) introduces a series of articles relating to collagen eye shields by describing the shields as similar to contact lenses. The shields are generally made of porcine scleral collagen which can be cross-linked in variable amounts in order to effect their rate of dissolution after insertion.

When put into the eye and hydrated, the collagen shields conform to the shape of the eye, but do not "suck on" the way vision corrective contact lenses do. As the collagen shields dissolve, they provide a layer of biologically compatible collagen solution which lubricates the surface of the eye, thereby minimizing rubbing of the eyelids on the cornea and fostering epithalial healing.

Kaufman, supra further reports that the collagen fibrils of the shields can trap, within their interstices, molecules of drug which are then held on the cornea by the shield. Both water soluble and water-insoluble drugs are suggested for use with collagen shields.

Some of the drugs which have actually been used with collagen shields are pilocarpine (Rubin et al., *J. Clin. Pharmacol. August–September,* 309 (1973); Aquauella et al., *J. Cataract Refract. Surg.* 14, 492 (1988); U.S. Pat. No. 4,164,559), tobramycin (Unterman et al., *Invest. Ophthalmol. Vis. Sci.* 29 (Suppl), 52 (1988); Unterman et al. *J. Cataract Refract. Surg.* 14, 500 (1988); O'Brien et al., *J. Cataract Refract. Surg.* 14, 505 (1988); Sawush et al., *Invest. Ophthalmol Vis. Sci.* 29 (Suppl), 228 (1988); Poland et al., *J. Cataract Refract. Surg.* 14, 489 (1988); Aquavella et al., supra), gentamicin (Aquavella et al., supra; U.S. Pat. No. 4,164,559) and flurbiprofen sodium (Aquavella et al., supra).

The drugs which have ben used with collagen eye shields are small, low molecular weight chemical entities. Large, high molecular weight substances, such as polysaccharides were not believed capable of incorporation in collagen, particularly for purposes of drug delivery. O'Brien et al., supra, have explicitly recognized that the uptake and release of a drug by a collagen shield depends upon the molecular weight and chemical structure of the drug. High molecular weight polysaccharides such as glucan were not believed to be capable of incorporation into, and delivery from a therapeutic collagen shield.

SUMMARY OF THE INVENTION

The present invention relates to therapeutic eye shields comprising collagen and glucan. The collagen serves as a drug delivery system for the therapeutic agent, glucan.

The glucan may be utilized in a particulate or soluble from. However, the soluble glucan is preferred.

The therapeutic effect of glucan is primarily to stimulate and activate macrophages. Therefore, the glucan/collagen therapeutic eye shields are used primarily to treat and prevent eye infections.

DETAILED DESCRIPTION OF THE INVENTION

The present invention relates to therapeutic eye shields used primarily to treat and prevent eye infections. The eye shields are composed of collagen and glucan. The collagen serves as a drug delivery system for the glucan, which is the therapeutic agent for treatment and prevention of infection.

Collagen is a polypeptide substance also known as ossein. Collagen has a molecular weight of about 130,000, and comprises about one-third of the total protein in mammalian organisms. It is the main constituent of skin and connective tissue, and is the organic substance of bones and teeth.

Collagen for use in eye shields is usually made from porcine scleral tissue (Poland et al., supra). Bausch & Lomb Pharmaceuticals, Inc. of Clearwater, Fla., provides commercially available collagen corneal shields under the name Bio-Cor ™ which are made from procine scleral tissue. These collagen eye shields dissolve on the eye to "provide a layer of biologically compatible collagen solution that seems to lubricate the surface of the eye, minimize rubbing of the lids on the cornea, and foster epithelial healing." Kaufman, supra.

A soluble telopeptide-poor collagen from calf skin is also suitable for use as an eye shield (Rubin et al., supra). This calf skin collagen is solubilized with a proteolytic enzyme such as pepsin and purified by known methods as described by Nishihara et al., *Trans. Amer. Soc. Artif. Int. Organs* 13, 243 (1967). This calf skin collagen is found to have minimal immunologic activity. It is also clear, viscous, has an optical rotation of $-410°$ and a glycine content of 33%, and consists of telopeptide-poor tropocollagen.

Other suitable collagens for the present eye shields include the succinylated or methylated telopeptide-poor collagens described in U.S. Pat. No. 4,164,559. Succinylation or methylation of collagen renders it soluble in a pH range of about 5.5 to about 9.0, whereas nonsuccinylated collagen and nonmethylated collagen are only soluble in the much narrower pH range of about 7.0 to about 7.5.

Succinylation of collagen also results in a large negative net charge at physiologic pH, thereby rendering the succinylated collagen receptive to positively charged therapeutic agents. Conversely, methylation of collagen results in a large positive net charge at physiologic pH, thereby rendering the methylated collagen receptive to negatively charged therapeutic agents such as phosphorylated glucan.

In accordance with the procedures set forth in U.S. Pat. No. 4,164,559, succinylated collagen and methylated collagen are prepared from calfskin, deer hide, cow hide or pig skin collagens. Dehaired and cleaned skin or hide is solubilized with a proteolytic enzyme such as pepsin. The solubilized collage is then precipitated at pH 7 after inactivation of the enzyme activity by caustic treatment at pH 10. The collagen is purified by repeated redissolution in acidic water (pH 2–4) and reprecipitation at pH 7.

Acylation of the amino groups with succinic anhydride yields the succinylated collagen. In contrast, esterification of the carboxyl groups by standard reaction with methanol yields the methylated collagen.

Other suitable collagens for the present invention include any of the above-described collagens which have been cross-linked. Conventional cross-linking treatments for collagen include the use of glutaraldehyde, ultraviolet radiation or gamma radiation.

Held within the interstices of the collagen of the inventive therapeutic eye shields is the therapeutic agent, glucan. Glucan is a high molecular weight (about 240,000) polysaccharide (Manners et al., supra), which is commonly isolated from the cell walls of *Saccharomyces cerevisiae*. Glucan is responsible for the cell rigidity, and under a scanning microscope can be seen as a spheroid approximately 5 μm in diameter (Baxter et al., supra).

As reported in U.S. Pat. No. 4,739,046, glucan is also available from the following sources: *Alicaligenes faecalis; Auricularia auricula-judae; Auricularia polytricha; Candida utilis; Cladesporium fulvum; Claviceps purpurea; Cochiliobolus sativus; Coriolus versicolor; Corlinellus shiitake; Corticium vagum; Grifola umbellata; Pichia fermentans; Poria cocos; Sclerotium coffeicolum; Sclerotium delp-*

*hnii; Sclerotium glucanium; Sclerotium rolsfi; Shizophyllum commune; Streptococcus salvarius; Stereum sanguinolentum;* and *Wingea robertsii.*

Glucan has a high proportion of β-(1,6)-glucosidic linkages (Manners et al., supra), and in its natural state is water insoluble (Sarko et al., supra). Upon hydrolysis, glucan yields predominantly, if not completely, D-glucose (Manners et al., supra).

Isolation of glucan from *Saccharomyces cerevisiae* is most commonly performed using the methods of Hassid et al., *J. Amer. Chem. Soc.* 63, 295 (1941) or those of DiLuzio et al., *Int. J. Cancer* 24, 773 (1979). The DiLuzio et al. method comprises a modification of the Hassid et al. procedure, starting with dry yeast suspended in a 3% aqueous solution of sodium hydroxide. The suspension is boiled, then cooled, and the supernatant is decanted. This heating, cooling and decanting procedure is repeated three times. The residue of the procedure is then acidified with concentrated hydrochloric acid and heated, cooled, and the supernatant decanted. This procedure of digestion with hydrochloric acid, heating, cooling and supernatant decanting is repeated twice, and then the residue is washed three times with 100° C. water and washed twice with 20° C. water.

The residue is then extracted for at least 24 hours with ethyl alcohol. A dark reddish-brown alcohol supernatant is aspirated from the residue, and the alcohol extraction is repeated until the supernatant is essentially colorless. The alcohol is then removed by washing the residue with hot water four times, and the particulate glucan is collected by centrifugation.

Particulate β-1,3-glucan can also be isolated from euglena cells as described in published Japanese patent application No. Sho 63 [1988]-71192. The method of obtaining the β-1,3-glucan involves increasing its concentration in euglena cells by adjusting the growth conditions of the euglena cells. Specifically, the concentration of β-1,3-glucan in euglena cells is increased by adjusting: (1) the carbon density in the medium; (2) the ratio of carbon to nitrogen; (3) acidity of the medium; (4) the temperature; and (5) the density of dissolved oxygen. More specifically, the carbon concentration of the carbon source in the culture medium is about 2 to 12 grams/liter; the atomic weight ratio of carbon to nitrogen (C/N) is about 10 to 30; the acidity at the time of multiplication is about pH 3 to 6; the temperature is about 25° to 34° C.; and the dissolved oxygen density is about 0.1 to 1.0 ppm.

The other ingredients of the culture medium are those which are conventional in the art, including saccharides, organic acids, alcohol and carbonate gases. Suitable euglenoids include *Euglena grassilis, Euglena billide* and *Euglena intermedia.*

The β-1,3-glucan is extracted from dried euglena cells using conventional techniques known in the art. About 1.15 to 1.25 grams of β-1,3-glucan are recovered per 1 gram of culture medium carbon using this method.

Soluble glucans have also been prepared, and are also suitable for use as the therapeutic agent of the present glucan/collagen eye shields. One such soluble glucan is produced using the method of Sasaki et al., *Gann* 67, 191 (1976) as modified by DiLuzio et al., *Int. J. Cancer* 24, 773 (1979). In this method, particulate glucan is heated with formic acid for about 40 minutes at 95°-100°. The formic acid is then removed by flash evaporation, and the residue is hydrolyzed with water in a boiling water bath. The solution is filtered, and the filtrate is flash evaporated to dryness. The filtering and evaporation procedure is repeated twice, and the resulting brown solid contains 60% glucose and 40% soluble glucan. Thin-layer chromatographic separation using mono-(glucose), di-(sucrose) and tri-(melezitose) saccharides as standards, reveals that the soluble glucan is a mixture of polysaccharides with varying chain lengths.

Another soluble glucan is described in U.S. Pat. No. 4,739,046. This is a soluble phosphorylated glucan derived form *Saccharomyces cerevisiae.* The solubility of this glucan is based on sufficient "relaxation" of the glucan triple helix to permit phosphorylation of each chain (or strand). Such "relaxation" is accomplished by dissolving particulate glucan in a highly polar solvent, such as dimethylsulfoxide (DMSO), in the presence of a strong chaotropic agent, such as urea. The resultant glucan is then reacted with phosphoric acid. More particularly, particulate glucan derived from *Saccharomyces cerevisiae* is suspended in a solution of 4 to 12M urea in DMSO with constant stirring. The urea "relaxes" hydrogen bonding along the polyglucose chain of glucan thus unfolding the molecule, and preventing the reformation of hydrogen bonds. The suspension is heated at about 50°-150° C., and phosphoric acid is added while continuing the constant stirring. A precipitate of soluble phosphorylated glucan forms in about one hour.

The precipitated phosphorylated glucan is recovered from the reaction mixture by cooling the mixture, and diluting the mixture with sufficient water to resuspend the precipitate. The resulting solution is filtered to remove any remaining precipitate, and molecularly sieved to remove all components of molecular weight less than about 10,000 daltons (i.e. to remove DMSO, urea and any unreacted phosphoric acid). A Millipore dialyzer/concentrator with a 10,000 daltons MW membrane filter and a large volume of dialyzing solution may be used for the molecular sieving. Following the molecular sieving, the resulting solution is concentrated and lyophilized to yield the soluble phosphorylated glucan as a fluffy powder.

An additional glucan which is suitable for the present invention is lentinan. Lentinan is a glucan which is isolated from the Japanese mushroom, *Lentines edodes* as described by Chihara et al., *Nature* 222, 687 (1969). Lentinan has primarily (1→3)-β-linkages, and a molecular weight of about one million (Sasaki et al., *Gann* 67, 191 (1976)). Lentinan may be solubilized by sonification (Kanai et al., *Japan J. Med. Sci. Biol.* 33, 283 (1980)).

Other suitable glucans are extracted from microorganisms using conventional techniques. Specifically, glucan is produced by *Sclerotium rolfsii* (ATCC ® No. 15206), extracellular glucan is produced by *Acremonium diospyri* (ATCC ® No. 9066) and *Monilinia fructigena* (ATCC ® No. 24976), and β-1,3-glucan is produced by *Aspergillus oryzae* (ATCC ® No. 48022) and *Pestalotiopsis sp.* (ATCC ® No. 56924).

Of all the suitable glucans for the present invention, the soluble glucans are preferred. This preference is based on the easier incorporation of soluble glucans into collagen to produce the glucan/collagen eye shields.

Glucan's therapeutic value derives from its ability to stimulate and activate macrophages of the reticuloendothielial system. Glucan also activates complement, as well as B cell lymphocytes. Of particular interest with regard to the present invention, it has been found that administration of glucan results in the following immunobiological responses: (1) enhanced proliferation of monocytes and macrophages (Diemann et al., *J. Exper. Med.* 149, 883 (1979); Ashworth et al., *Exper. Molec. Pathol. Supp.* 1, 83 (1963)); (2) enhanced macrophage secretory activity (Bärlin et al., Heterogeneity of Mononuclear Phagocytes, Forster and Landy, eds., Academic Press, New York, pp. 243-252 (1981)); (3) increased macrophage size (Patchen et al., *Exper. Hematol.* 8, 409 (1980)); (4) enhancement of macrophage phagocytosis (Riggi et al., *Am. J. Physiol.* 200, 297 (1961)); (5) enhancement of macrophage adherence and chemotactic activity (Niskanen et al., *Cancer Res.* 38, 1406 (1978)); and (6) enhancement of complement activation (Glovsky et al., *J. Reticuloendothel. Soc.* 33, 401 (1983)).

The above immunobiological responses result in enhanced host resistance to infectious diseases caused by bacteria, viruses, fungi and parasitic organisms. Specific microorganisms for which glucan administration enhances host resistance include the bacteria *Eschericheria coli, Staphylococcus aureus, Francisella tularensis, Mycobacterium leprae, Streptococcus pneumoniae, Candida albicans* and *Sporotrichum schenckii;* the viruses Venezuelan equine encephalomyelitis virus, Rift Valley fever virus, murine hepatitis virus, frog virus III and Herpes simplex virus I and II; and the parasites *Leishmania donovani* and *Schistosoma mansoni* (DiLuzio, *Trends in Pharmacol. Sci.* 4, 344 (1983)).

Glucans also accelerate reepithelialization, as well as increasing the production of fibroblasts and thereby increasing fibrogenesis (Wolk et al., *Medical Biology* 63, 73 (1985); Liebonich et al., *J. Reticuloendothel Soc.* 27, 1 (1980)). When used as the therapeutic agent in the inventive therapeutic eye shields, the application of glucan after eye surgery will promote healing of the incision by its acceleration of reepithelialization. Eye surgery for which glucan application would be suitable to promote reepithelialization includes corneal transplantation, radial keratotomy and epikeratophakia. This reepithelialization property of glucan can also be used to promote the healing of wounds to the eye.

Prior to its use in the present glucan/collagen therapeutic eye shields, glucan had not been used for ophthalmic purposes, or in ophthalmic preparations. Glucan alone does not have sufficient gelling (setting) properties to be formed into a suitable eye shield. Similarly, glucan alone is not satisfactory for application to the eye, because the tearing of the eye washes the glucan away from the site of therapeutic action. Therefore, the inventors combined a therapeutically effective amount of glucan with collagen to make the present therapeutic eye shields. The collagen has the required gelling properties, and prevents the glucan from being washed away from the site of therapeutic action in the eye. The inventors also found that the combination of glucan and collagen had a more than additive effect on ophthalmic healing when compared to the ophthalmic healing effect of glucan or collagen alone.

The therapeutic glucan/collagen eye shields of the present invention are most commonly prepared by one of two suitable methods. In one method, collagen eye shields are produced by conventional techniques, and then, the glucan is added after formation of the shield. In the other method, the glucan and the collagen are mixed together, and then the mixture is molded into the therapeutic eye shield.

In order to prepare a collagen eye shield, a collagen solution is prepared by solubilizing a collagen source, such as calf skin or procine scleral tissue, with a proteolytic enzyme, such as pepsin. This collagen solution is then purified by conventional techniques such as those taught by Nishihara et al., *Trans. Amer. Soc. Artif. Int. Organs* 13, 243 (1967). The purified collagen solution is then poured into a suitable mold and allowed to dry and set. Suitable molds are commonly made from methacrylate polymers and yield eye shields about 0.0125 mm to about 0.0725 mm thick with a base curve of about 9.0 mm and a diameter of about 14.5 mm.

The dried collagen eye shields are then rehydrated with a glucan solution, and the glucan becomes embedded within the interstices of the collagen molecules. The glucan solution can also be used to rehydrate commercially available collagen eye shields such as Bio-Cor ™ collagen corneal shields from Bausch & Lomb Pharmaceuticals, Inc. of Clearwater, Fla. The dried collagen eye shields are preferably rehydrated immediately before placement on the eye.

In the other method for producing the glucan/collagen therapeutic eye shields, the glucan and collagen are molded together to form the shields. A purified collagen solution is prepared as explained above, and glucan is admixed therein. The glucan may be in either particulate form or in the form of a solution, although a glucan solution is preferred. The glucan/collagen admixture is then poured into molds as explained above, and allowed to dry and set to yield dried glucan/collagen therapeutic eye shields. These eye shields can be rehydrated with physiologic saline.

The concentration of glucan present in the therapeutic eye shields is sufficient to deliver between about 0.1 mg and about 5.0 mg per 12 hour period. Depending on the degree of crosslinking of the collagen in the eye shield, the eye shield will dissolve on the patient's eye over a period of between about 2 hours and about 72 hours. Most commonly, the therapeutic eye shields dissolve on the eye over a time period from about 2 hours to about 12 hours. Therefore, the amount of glucan in the therapeutic eye shield is adjusted accordingly, in order for the eye shield to deliver a therapeutic dose over the time during which it dissolves on the eye.

The therapeutic eye shields comprise from about 50% to about 80% by weight collagen and from about 20% to about 50% by weight glucan in the dehydrated form. Oftentimes, there is also a slight amount of moisture present in the eye shields. The amount of moisture present is up to about 10% by weight.

Once rehydrated with either physiologic saline or glucan solution, the glucan/collagen therapeutic eye shields are placed on the patient's eye where they will dissolve over time. As mentioned above, the time over which the shields dissolve is determined by the degree of crosslinking of the collagen.

As the collagen dissolves, the glucan molecules are gradually released from the interstices of the collagen molecules. The maintenance of constant glucan concentration in conjunction with the increased time of contact with the wound or incision permits increased glucan penetration into the cornea and anterior chamber of the eye.

In addition to therapeutic benefits of glucan on the eye (i.e. antiinfective properties and wound healing properties), the collagen itself also has beneficial properties for the wounded eye or the eye which has been subjected to surgery. Following radial keratotomy corneal incision, the application of a collagen eye shield to the eye results in the following:

(1) the speed of epithelial healing is increased;

(2) there is a reduction of stromal edema at the incision site;

(3) the shield appears to protect keratocytes adjacent to the incision and keratocyte reaction is thereby diminished;

(4) inflammatory reaction and polymorphonucleocyte infiltration of the incision site are diminished; and (5) surface epithelial bonding is normalized. (Marmer, *J. Cataract Refract. Surg.* 14, 496 (1988)).

After manufacture, the therapeutic eye shields may be stored in their dried condition at room temperature until they need to be used. For use after eye surgery or a wounding of the eye, the therapeutic shields first must be rehydrated. In the preferred case where the shield already contains glucan, the dried shield is rehydrated for about twenty minutes in physiologic saline. A similar twenty-minute rehydration with a glucan solution is performed with the eye shields made of collagen alone.

The therapeutic eye shields are generally placed on the eye with the aid of a local anesthetic such as lidocaine. The local anesthetic is generally needed due to the traumatized condition of the eye which has been subjected to an incision or a wound, rather than because of properties of the therapeutic shield itself. The therapeutic eye shields are comfortable on the eye, and are well tolerated without significant adverse effects. After placement of the shields on the eye, the eye may be patched or left unpatched, although patching of the eye is preferred, at least for about the first twenty-four hours after application of the therapeutic shield.

When first applied to the eye, the therapeutic shield acts as a hydrophilic bandage which serves to protect the corneal surface. However, as the therapeutic shield comes in contact with the tears, a proteolytic and hydrolytic degradation process begins to take place, which eventually yields a relatively thick, mucus-like, collagenous film which covers the entire ocular surface. The therapeutic shield and the collagenous film that results therefrom act as a reservoir of glucan, from which the glucan is passively released at a substantially constant rate. As biodegradation of the therapeutic shield continues, there is increased lubrication of the eye from the degrading collagen with a continued release of glucan.

After the therapeutic shield has been applied to the eye, the reservoir of glucan therein can be supplemented by the application of glucan solution used as ophthalmic drops. Other compatible therapeutic agents may also be applied to the therapeutic shield on the eye as indicated by the patient's condition.

The therapeutic shields have a high permeability to oxygen at the time of application (approximately twice that of conventional hydrophilic contact lenses—Aquavella et al., *J. Cataract Refract. Surg.* 14, 492 (1988)), which increases over time as the collagen of the shield degrades. The biodegradation of the shield offers the additional advantage of eliminating any need for removal of the therapeutic shield once it has been applied to the eye.

The invention is further illustrated by the following non-limiting examples.

EXAMPLE 1

Glucan/Collagen Therapeutic Eye Shields Made with Particulate Glucan

Porcine scleral collagen is prepared by the method described in U.S. Pat. No. 4,164,559. Five kilograms of fresh pigskin is dehaired and cleaned by shaving. The pigskin is then cut to small pieces and added to ten liters of hydrochloric acid-acidified water at pH 2.5. One gram of pepsin is then added to the acidified water, and the whole is kept at 20° C. for five days with intermittent stirring. The resulting viscous solubilized collagen is filtered through cheesecloth and sufficient sodium hydroxide is added thereto to adjust the pH to 10. The collagen is allowed to stand for twenty-four hours at 4° C. to inactivate the pepsin. Hydrochloric acid is then added to the collagen to adjust the pH to 7 and the collagen precipitate is recovered by centrifugation The collagen is then purified by redissolution in the acidic aqueous solution, and reprecipitation at pH 7.

Particulate glucan is prepared by the method of DiLuzio et al., *Inst. J. Cancer* 24, 773 (1979). A suspension of 540 grams of dry yeast in three liters of an aqueous 3% sodium hydroxide solution is heated in a boiling water bath for four hours, cooled for eight hours, and then the supernatant is decanted. This procedure is repeated three times, and the residue is then acidified with 800 milliliters of concentrated hydrochloric acid and two liters of 3% hydrochloric acid. The acid suspension is heated in a boiling water both for four hours, cooled for eight hours, and the supernatant is decanted. The residue is then further digested with three liters of 3% hydrochloric acid at 100° C. for four hours, allowed to cool for eight hours, and decanted. This 3% hydrochloric acid digestion is repeated twice, and then the residue is washed three times with distilled water at 20° C. and washed twice with distilled water at 100° C. The residue is mixed with one liter of ethyl alcohol and allowed to stand for twenty-four hours. A dark reddish-brown alcohol supernatant is aspirated from the residue and discarded, and the alcohol extraction is repeated three times until the supernatant is essentially colorless. The alcohol is removed from the residue by washing with hot water four times, and the particulate glucan is collected by centrifugation.

Three grams of collagen is then dissolved in 200 milliliters of hydrochloric acid in acidified water at pH 3, and 800 milligrams of particulate glucan is mixed with the collagen. The pH of the mixture is adjusted to 7 by the addition of sodium hydroxide, and the mixture is de-aerated by vacuum for thirty minutes The mixture is then poured into polymethylmethacrylate molds and allowed to air dry for twenty-four hours. The resulting therapeutic eye shields are 0.050 millimeters thick with a diameter of 14.5 millimeters and a base curve of 9.0 millimeters. Each therapeutic eye shield weights 10.0 milligrams and contains 7.0 milligrams collagen, 2.0 milligrams glucan and 1.0 milligram moisture.

EXAMPLE 2

Glucan/Collagen Therapeutic Eye Shields Made with Soluble Glucan

Porcine scleral collagen is prepared as described in Example 1.

Soluble glucan is prepared by the method of DiLuzio et al., *Int. J. Cancer* 24, 773 (1979). Ten grams of particulate glucan as prepared in Example 1 is heated with 182 milliliters of 90% formic acid at 100° C. for forty minutes, after which the formic acid is removed by flash evaporation. The residue is hydrolyzed with 500 milliliters of water in a boiling water both for three hours. The solution is then filtered through a fine sintered blass funnel, and the filtrate is flash-evaporated to dryness. This hydrolysis and filtering procedure is repeated twice, resulting in a brown solid containing 60% glucose and 40% soluble glucan.

As in Example 1, three grams of collagen is dissolved in 200 milliliters acidified water at pH 3. However, two grams of the above brown solid is mixed with the collagen in order to achieve the proper concentration of glucan (i.e. only 40% of the brown solid is soluble glucan). The pH of the mixture is then adjusted to 7 by the addition of sodium hydroxide, and the mixture is de-aerated by vacuum for thirty minutes The mixture is poured into polymethylmethacrylate molds to form therapeutic eye shields as described in Example 1. Each eye shield weighs 10.0 milligrams and contains 5.50 milligrams collagen, 1.50 milligrams glucan, 2.30 milligrams glucose and 0.70 milligram moisture.

EXAMPLE 3

Glucan/Collagen Therapeutic Eye Shields Made By Rehydrating Collagen Eye Shields with a Glucan Solution Porcine scleral collagen is prepared as described in Example 1. The collagen is formed into eye shields by first dissolving three grams of collagen in 200 milliliters of hydrochloric acid in acidified water at pH 3. Then, the pH of the solution is adjusted to 7 by addition of sodium hydroxide, and the solution is de-aerated by vacuum for thirty minutes. Finally, the collagen solution is poured into polymethylmethacrylate molds and air-dried for twenty-four hours to yield collagen eye shields which are 0.050 millimeter thick, have a diameter of 14.5 millimeters and a base curve of of 9.0 millimeters.

Soluble glucan is prepared as described in Example 2, and two grams of the glucan is dissolved in 200 millimeters of distilled water. The collagen eye shields are then rehydrated in the glucan solution for twenty-four hours to yield glucan/collagen therapeutic eye shields which weigh 10.0 milligrams each, and contain 5.50 milligrams collagen, 1.50 milligrams glucan, 2.30 milligrams glucose and 0.70 milligram moisture.

EXAMPLE 4

Glucan/Collagen Therapeutic Eye Shields Made with Soluble Phosphorylated Glucan

Porcine scleral collagen is prepared as described in Example 1.

Soluble phosphorylated glucan is prepared as described in U.S. Pat. No. 4,739,046. One gram of particulate glucan as prepared in Example 1 is added to a solution of 18 grams of urea (8M) in 50 milliliters of dimethylsulfoxide (DMSO) to form a finely divided suspension. The suspension is heated to 100° C., and 10 milliliters of 85% phosphoric acid is slowly added dropwise. The mixture is maintained at 100° C. for eight hours by means of a boiling water bath. A precipitate forms during the heating.

After the heating, the mixture is cooled to room temperature and the precipitate is resuspended by the addition of 200 milliliters of distilled water. The mixture is then filtered through course, medium and fine sintered funnels, and the resulting solution is molecularly sieved using a Millipore dialyzer/concentration with a 10,000 daltons MW membrane filter to remove low molecular weight fractions of glucose, DMSO and urea. The remaining solution containing soluble phosphorylated glucan is then concentrated and lyophilized using conventional techniques.

Therapeutic eye shields, each of which contains 7.0 milligrams collagen, 2.0 milligrams glucan and 1.0 milligram moisture are then prepared from the porcine scleral collagen and phosphorylated glucan as described in Example 1.

EXAMPLE 5

Glucan/Collagen Therapeutic Eye Shields Made from Glucan Derived from Euglena Cells Porcine scleral collagen is prepared as described in Example 1.

Glucan is derived from specially grown euglena cells as described in published Japanese patent application No. Sho 63 [1988]-71192. *Euglena grassilis* cells are grown in a conventional culture medium containing saccharides, organic acids, alcohols and carbonate gases. However, the following specific adjustments are made to the growing conditions of the cells: (1) the carbon concentration of the carbon source of the medium is 10 grams/liter; (2) the atomic weight ratio of carbon to nitrogen in the medium is 25; (3) the acidity of the medium at the time of cell multiplication is pH 5; (4) the temperature is maintained at 30° C.; and (5) the dissolved oxygen density of the medium is 0.80 ppm. *Euglena grassilis* cells grown under these conditions contain a high concentration of $\beta$-1,3-glucan.

The glucan is extracted from the cells using conventional techniques, and therapeutic eye shields are produced from the collagen and glucan as described in Example 1. Each 10.0 milligram eye shield contains 7.0 milligrams collagen, 2.0 milligrams glucan and 1.0 milligram moisture.

EXAMPLE 6

Glucan/Collagen Therapeutic Eye Shields Made with Soluble Phosphorylated Glucan and Methylated Collagen Soluble phosphorylated glucan is prepared as described in Example 3. Such phosphorylated glucan is negatively charged when in aqueous solution.

Methylated collagen is prepared as described in U.S. Pat. No. 4,164,559. Ten grams of porcine scleral collagen as prepared in Example 1 is immersed in two liters of dehydrated methanol containing 0.1N hydrochloric acid at room temperature in a sealed vessel for seven days. The methylated collagen is then dried with a vacuum. The methylated collagen has a net positive charge in aqueous solution.

The methylated collagen and phosphorylated glucan are mixed and molded as described in Example 3 to form therapeutic eye shields. Each eye shield weighs 10.0 milligrams and contains 7.0 milligrams methylated collagen, 2.0 milligrams phosphorylated glucan and 1.0 milligram moisture. The opposite charges of the methylated collagen (net positive charge) and the phosphorylated glucan (net negative charge) create an attractive interaction which prevents rapid release of glucan from the eye shield.

EXAMPLE 7

Use of Glucan/Collagen Therapeutic Shields Following Radial Keratotomy Corneal Incisions Radial keratotomy (RK) is performed on twenty-eight rabbits weighing from 2.5 kilograms to 3.0 kilograms. The surgery is performed under local anesthesia, and each rabbit has a partial-thickness, nonperforating incision which is 4.5 millimeters long and 0.4 millimeter deep beginning at the corneal periphery and directed centrally toward the optic zone.

The rabbits are divided into seven groups of four rabbits each. Therapeutic eye shields from Examples 1-5 above are hydrated for 30 minutes in physiologic saline. Then therapeutic eye shields of Example 1 are applied to the eyes of the rabbits in Group 1, the eye shields of Example 2 are applied to the eyes of the rabbits Group 2, the eye shields of Example 3 are applied to the eyes of the rabbits in Group 3, the eye shields of Example 4 are applied to the eyes of the rabbits in Group 4, the eye shields of Example 5 are applied to the eyes of the rabbits in Group 5, collagen eye shields without a therapeutic agent are applied to the eyes of the rabbits in Group 6 which serve as controls, and the rabbits in Group 7 also serve as controls and do not receive an eye shield postoperatively.

All of the eye shields have dissolution rates of twelve hours, because they are made with non-crosslinked collagen. The rabbits eyes are examined after six hours, and a relatively thick collagenous film is observed over the entire ocular surface. After twelve hours, the collagenous film has virtually disappeared from the ocular surface. At twenty-four hours after application of the eye shields, the rabbits in Groups 1-5 display intact corneal epithelium and no punctuate staining. The only epithelial edema present is confined to areas adjacent the sutures.

The control rabbits in Group 6 (collagen eye shields without therapeutic agent) show slightly more epithalial edema than the rabbits in Groups 1-5. However, the control rabbits without eye shields (Group 7) show a greater degree of epithelial edema and a slower healing of the epithelium. There are no infections noted in either the control group or the experimental groups.

EXAMPLE 8

Treatment of Eye Infection with Glucan/Collagen Therapeutic Eye Shields

Twenty-eight rabbits are divided into seven groups with four rabbits in each group. Each rabbit weighs from 2.5 kilograms to 3.0 kilograms. A clinical isolate of *Staphylococcus aureus* is diluted with physiologic saline to provide $2.5 \times 10^8$ viable cells per 0.5 milliliters. Each rabbit has 0.5 milliliters of *S. aureus* solution applied dropwise to its right eye in order to stimulate infection.

Glucan/collagen therapeutic eye shields from Examples 1-5 above are applied to the infected right eye of each rabbit in Groups 1-5, respectively, six hours after instillation of the *S. aureus* solution. The rabbits of Group 6 serve as controls and have a plain collagen eye shield applied to their right eyes, while the rabbits of Group 7 serve as additional controls and do not have any eye shield applied to their right eyes.

The experimental rabbits of Groups 1-5 display resistance to the *S. aureus* infection of their right eyes. In contrast, the control rabbits of Group 6 show slight *S. aureus* infection in their right eyes, and all of the rabbits in control Group 7 display acute infection with *S. aureus*.

While the invention has been disclosed by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

What is claimed is:

1. A therapeutic eye shield comprising a mixture of a therapeutically effective amount of glucan, and sufficient collagen to hold the glucan and form said therapeutic eye shield of sufficient dimensions to substantially cover a cornea when applied to an eye.

2. The therapeutic eye shield of claim 1 wherein said glucan is present from about 20% to about 50% by weight of said shield.

3. The therapeutic eye shield of claim 2 wherein said collagen is present from about 50% to about 80% by weight of said shield.

4. The therapeutic eye shield of claim 1 wherein said collagen is crosslinked.

5. The therapeutic eye shield of claim 3 wherein said collagen is crosslinked.

6. The therapeutic eye shield of claim 1 wherein said glucan is a water soluble glucan.

7. The therapeutic eye shield of claim 3 wherein said glucan is a water soluble glucan.

8. The therapeutic eye shield of claim 6 wherein said water soluble glucan is phosphorylated glucan.

9. The therapeutic eye shield of claim 7 wherein said water soluble glucan is phosphorylated glucan.

10. The therapeutic eye shield of claim 9 wherein said collagen is methylated collagen.

11. The therapeutic eye shield of claim 10 wherein said collagen is methylated collagen.

12. The therapeutic eye shield of claim 1 wherein said eye shield is substantially oval in shape, has a thickness from about 0.0125 millimeter to about 0.0725 millimeter and a base curve of about 9.0 millimeters.

13. The therapeutic eye shield of claim 3 wherein said eye shield is substantially oval in shape, has a thickness from about 0.0125 millimeter to about 0.0725 millimeter and a base curve of about 9.0 millimeters.

14. The therapeutic eye shield of claim 5 wherein said eye shield is substantially oval in shape, has a thickness from about 0.0125 millimeter to about 0.0725 millimeter and a base curve of about 9.0 millimeters.

15. The therapeutic eye shield of claim 7 wherein said eye shield is substantially oval in shape, has a thickness from about 0.0125 millimeter to about 0.0725 millimeter and a base curve of about 9.0 millimeters.

16. The therapeutic eye shield of claim 10 wherein said The therapeutic eye shield of claim 1 wherein said eye shield is substantially oval in shape, has a thickness from about 0.0125 millimeter to about 0.0725 millimeter and a base curve of about 9.0 millimeters.

17. The therapeutic eye shield of claim 12 wherein said eye shield is substantially oval in shape, has a thickness from about 0.0125 millimeter to about 0.0725 millimeter and a base curve of about 9.0 millimeters.

18. A method of treating eye infections by applying the therapeutic eye shield of claim 1 to an infected eye.

19. A method of enhancing healing of an eye after surgery or wounding by applying the therapeutic eye shield of claim 1 to an eye after ophthalmic surgery or wounding.

* * * * *

UNITED STATES PATENT AND TRADEMARK OFFICE
CERTIFICATE OF CORRECTION

PATENT NO.   :   4,946,450
DATED        :   August 7, 1990
INVENTOR(S)  :   Robert L. ERWIN It is certified that error appears in the above-identified patent and that said Letters Patent is hereby corrected as shown below:

Column 14, line 33:

the dependency of claim 10 should be changed from claim 9 to claim 8;

Column 14, line 35:

the dependency of claim 11 should be changed from claim 10 to claim 9;

Column 14, line 53:

the dependency of claim 16 should be changed from claim 10 to claim 9; and

Column 14, line, 58:

the dependency of claim 17 should be changed from claim 12 to claim 11.

Signed and Sealed this

Thirty-first Day of March, 1992

Attest:

HARRY F. MANBECK, JR.

*Attesting Officer*          *Commissioner of Patents and Trademarks*